United States Patent
Verhaeghe et al.

(10) Patent No.: US 10,435,729 B2
(45) Date of Patent: Oct. 8, 2019

(54) SUCROSE PHOSPHORYLASE FOR THE PRODUCTION OF KOJIBIOSE

(71) Applicant: Universiteit Gent, Ghent (BE)

(72) Inventors: Tom Verhaeghe, Zwevegem (BE); Karel De Winter, Zottegem (BE); Tom Desmet, Nevele (BE)

(73) Assignee: UNIVERSITEIT GENT, Ghent (BE)

( * ) Notice: Subject to any disclaimer, the term of this patent is extended or adjusted under 35 U.S.C. 154(b) by 47 days.

(21) Appl. No.: 15/526,402

(22) PCT Filed: Nov. 12, 2015

(86) PCT No.: PCT/EP2015/076397
§ 371 (c)(1),
(2) Date: May 12, 2017

(87) PCT Pub. No.: WO2016/075219
PCT Pub. Date: May 19, 2016

(65) Prior Publication Data
US 2017/0314052 A1    Nov. 2, 2017

(30) Foreign Application Priority Data

Nov. 14, 2014    (EP) .................................... 14193238

(51) Int. Cl.
| | | |
|---|---|---|
| *C12N 9/10* | (2006.01) | |
| *C12P 19/12* | (2006.01) | |
| *C12N 1/20* | (2006.01) | |
| *C12N 15/00* | (2006.01) | |
| *C07H 21/04* | (2006.01) | |
| *C12P 19/18* | (2006.01) | |
| *C12N 15/63* | (2006.01) | |

(52) U.S. Cl.
CPC ............ *C12P 19/18* (2013.01); *C12N 9/1051* (2013.01); *C12N 15/63* (2013.01); *C12P 19/12* (2013.01); *C12Y 204/01007* (2013.01)

(58) Field of Classification Search
None
See application file for complete search history.

(56) References Cited

FOREIGN PATENT DOCUMENTS

WO    2011/124538    10/2011

OTHER PUBLICATIONS

Studer. Residue mutations and their impact on protein structure and function: detecting beneficial and pathogenic changes. Residue mutations and their impact on protein structure and function: detecting beneficial and pathogenic changes. Biochem. J. (2013) 449, 581-594.*

Kawasaki. Cloning and expression in *Escherichia coli* of sucrose phosphorylase gene from Leuconostoc mesenteroides No. 165. Biosci Biotechnol Biochem. Feb. 1996;60(2):322-4.*

Goedl. Sucrose phosphorylase: a powerful transglucosylation catalyst for synthesis of a-D-glucosides as industrial fi ne chemicals Biocatalysis and Biotransformation, Jan.-Feb. 2010; 28(1): 10-21.*

Kitao, S. et al., "Formation of Kojibiose and Nigerose by Sucrose Phosphorylase", Bioscience, Biotechnology, and Biochemistry, vol. 58(4), pp. 790-791, 1994.

Luley-Goedl, C. et al., "Regioselective O-glucosylation by sucrose phosphorylase: a promising route for functional diversification of a range of 1,2-propanediols", Carbohydrate Research, vol. 345, pp. 1736-1740, 2010.

Desmet, T. et al., "Broadening the synthetic potential of disaccharide phosphorylases through enzyme engineering", Process Biochemistry, vol. 47, pp. 11-17, 2012.

Desmet, T. et al., "Enzymatic Glycosylation of Small Molecules: Challenging Substrates Require Tailored Catalysts", Chemistry—A European Journal, vol. 18, pp. 10786-10801, 2012.

International Search Report dated Mar. 1, 2016 in International (PCT) Application No. PCT/EP2015/076397.

T. Verhaeghe, et al.: "Mapping the Acceptor Site of Sucrose Phosphorylase from Bifidobacterium Adolescentis by Alanine Scanning", Journal of Molecular Catalysis B: Enzymatic, vol. 96, 2013, pp. 81-88.

K. De Winter, et al.: "An Imprinted Cross-Linked Enzyme Aggregate (iCLEA) of Sucrose Phosphorylase: Combining Improved Stability with Altered Specificity", International Journal of Molecular Sciences, vol. 13, 2012, pp. 11333-11342.

A. Cerdobbel, et al.: "Increasing the Thermostability of Sucrose Phosphorylase by a Combination of Sequence- and Structure-Based Mutagenesis", Protein Engineering Design and Selection, vol. 24, No. 11, 2011, pp. 829-834.

Written Opinion of the International Searching Authority dated Mar. 1, 2016 in International (PCT) Application No. PCT/EP2015/076397.

* cited by examiner

*Primary Examiner* — Yong D Pak
(74) *Attorney, Agent, or Firm* — Wenderoth, Lind & Ponack, L.L.P.

(57) ABSTRACT

The present invention relates to the production of the disaccharide kojibiose which is known to be a powerful prebiotic. The invention indeed discloses the generation of genetically modified sucrose phosphorylases which convert—via a transglycosylation reaction—sucrose into kojibiose in a very efficient manner. Hence, the present invention relates to a cost-effective production method of kojibiose which is useful within industry.

10 Claims, No Drawings
Specification includes a Sequence Listing.

SEQUENCE LISTING

<160> NUMBER OF SEQ ID NOS: 2

<210> SEQ ID NO 1
<211> LENGTH: 504
<212> TYPE: PRT
<213> ORGANISM: Bifidobacterium adolescentis

<400> SEQUENCE: 1

```
Met Lys Asn Lys Val Gln Leu Ile Thr Tyr Ala Asp Arg Leu Gly Asp
1               5                   10                  15

Gly Thr Ile Lys Ser Met Thr Asp Ile Leu Arg Thr Arg Phe Asp Gly
            20                  25                  30

Val Tyr Asp Gly Val His Ile Leu Pro Phe Phe Thr Pro Phe Asp Gly
        35                  40                  45

Ala Asp Ala Gly Phe Asp Pro Ile Asp His Thr Lys Val Asp Glu Arg
    50                  55                  60

Leu Gly Ser Trp Asp Asp Val Ala Glu Leu Ser Lys Thr His Asn Ile
65                  70                  75                  80

Met Val Asp Ala Ile Val Asn His Met Ser Trp Glu Ser Lys Gln Phe
                85                  90                  95

Gln Asp Val Leu Ala Lys Gly Glu Glu Ser Glu Tyr Tyr Pro Met Phe
            100                 105                 110

Leu Thr Met Ser Ser Val Phe Pro Asn Gly Ala Thr Glu Glu Asp Leu
        115                 120                 125

Ala Gly Ile Tyr Arg Pro Arg Pro Gly Leu Pro Phe Thr His Tyr Lys
    130                 135                 140

Phe Ala Gly Lys Thr Arg Leu Val Trp Val Ser Phe Thr Pro Gln Gln
145                 150                 155                 160

Val Asp Ile Asp Thr Asp Ser Asp Lys Gly Trp Glu Tyr Leu Met Ser
                165                 170                 175

Ile Phe Asp Gln Met Ala Ala Ser His Val Ser Tyr Ile Arg Leu Asp
            180                 185                 190

Ala Val Gly Tyr Gly Ala Lys Glu Ala Gly Thr Ser Cys Phe Met Thr
        195                 200                 205

Pro Lys Thr Phe Lys Leu Ile Ser Arg Leu Arg Glu Glu Gly Val Lys
    210                 215                 220

Arg Gly Leu Glu Ile Leu Ile Glu Val His Ser Tyr Tyr Lys Lys Gln
225                 230                 235                 240

Val Glu Ile Ala Ser Lys Val Asp Arg Val Tyr Asp Phe Ala Leu Pro
                245                 250                 255

Pro Leu Leu Leu His Ala Leu Ser Thr Gly His Val Glu Pro Val Ala
            260                 265                 270

His Trp Thr Asp Ile Arg Pro Asn Asn Ala Val Thr Val Leu Asp Thr
        275                 280                 285
```

```
His Asp Gly Ile Gly Val Ile Asp Ile Gly Ser Asp Gln Leu Asp Arg
            290                 295                 300

Ser Leu Lys Gly Leu Val Pro Asp Glu Asp Val Asp Asn Leu Val Asn
305                 310                 315                 320

Thr Ile His Ala Asn Thr His Gly Glu Ser Gln Ala Ala Thr Gly Ala
                325                 330                 335

Ala Ala Ser Asn Leu Asp Leu Tyr Gln Val Asn Ser Thr Tyr Tyr Ser
                340                 345                 350

Ala Leu Gly Cys Asn Asp Gln His Tyr Ile Ala Ala Arg Ala Val Gln
                355                 360                 365

Phe Phe Leu Pro Gly Val Pro Gln Val Tyr Tyr Val Gly Ala Leu Ala
            370                 375                 380

Gly Lys Asn Asp Met Glu Leu Leu Arg Lys Thr Asn Asn Gly Arg Asp
385                 390                 395                 400

Ile Asn Arg His Tyr Tyr Ser Thr Ala Glu Ile Asp Glu Asn Leu Lys
                405                 410                 415

Arg Pro Val Val Lys Ala Leu Asn Ala Leu Ala Lys Phe Arg Asn Glu
            420                 425                 430

Leu Asp Ala Phe Asp Gly Thr Phe Ser Tyr Thr Thr Asp Asp Asp Thr
            435                 440                 445

Ser Ile Ser Phe Thr Trp Arg Gly Leu Thr Ser Gln Ala Thr Leu Thr
450                 455                 460

Phe Glu Pro Lys Arg Gly Leu Gly Val Asp Asn Thr Thr Pro Val Ala
465                 470                 475                 480

Met Leu Glu Trp Glu Asp Ser Ala Gly Asp His Arg Ser Asp Asp Leu
                485                 490                 495

Ile Ala Asn Pro Pro Val Val Ala
            500

<210> SEQ ID NO 2
<211> LENGTH: 1512
<212> TYPE: DNA
<213> ORGANISM: Bifidobacterium adolescentis

<400> SEQUENCE: 2
atgaaaaata aagtccaact gattacctat gcggatcgtc tgggtgatgg caccattaaa      60
agcatgacgg acatcctgcg tacccgcttt gatggcgttt atgacggtgt ccacattctg     120 ccgttttca ccccgtttga tggcgccgac gcaggtttcg atccgatcga ccataccaaa      180
gttgatgaac gtctgggtag ctgggatgac gtcgccgaac tgtctaaaac ccacaacatt     240
atggtggatg caatcgttaa tcacatgtca tgggaatcga acagttccaa gatgttctg      300 gccaaaggcg aagaatcaga atattacccg atgtttctga ccatgagcag cgtgttcccg     360
aacggtgcca cggaagaaga cctggcaggc atttatcgtc gcgtccgggg tctgccgttt     420
acccactaca aattcgcagg caaaacgcgt ctggtctggg tgtcttttac cccgcagcaa     480
gtggacatcg atacggacag tgataaaggt tgggaatatc tgatgtccat tttcgaccaa     540
atggcggcca gccatgtgtc ttatatccgc ctggatgcgg ttggctacgg tgccaaagaa     600
gcaggcacca gttgctttat gaccccgaaa acgttcaaac tgatttcccg tctgcgcgaa     660
gaaggcgtga aacgcggtct ggaaattctg atcgaagtcc acagctatta caaaaaacag     720
gtggaaatcg cgtctaaagt ggatcgcgtt tatgactttg ccctgccgcc gctgctgctg     780
catgccctga gtaccggcca cgtcgaaccg gtggcccatt ggacggatat tcgtccgaac     840
```

```
aatgctgtta ccgtcctgga tacgcatgac ggcatcggcg ttattgatat cggttcagat    900
cagctggacc gctcgctgaa aggtctggtg ccggacgaag atgtggataa cctggtgaat    960
acgattcatg cgaacaccca cggcgaatca caggcagcta ccggtgcggc ggcatcgaac   1020
attgatctgt actcggttaa tagtacctac tactccgctc tgggctgtaa cgatcagcac   1080
tacatcgctg cgcgtgcggt gcagtttttc ctgccgggtg ttccgcaagt ctattacgtg   1140
ggcgccctgg caggtaaaaa tgatatggaa ctgctgcgca aaaccaacaa tggtcgtgac   1200
attaaccgcc attattacag cacggccgaa atcgatgaaa atctgaaacg tccggtggtt   1260
aaagcactga acgctctggc gaaatttcgc aatgaactgg atgcttttga cggcaccttc   1320
tcatatacca cggatgacga tacgagtatt tcctttacct ggcgtggtga aacgtcgcag   1380
gccaccctga cgttcgaacc gaaacgcggc ctgggtgttg ataataccac gccggtcgca   1440
atgctggaat gggaagacag tgctggtgac catcgctccg acgacctgat cgctaatccg   1500
ccggttgttg cg                                                      1512
```

SUCROSE PHOSPHORYLASE FOR THE PRODUCTION OF KOJIBIOSE

TECHNICAL FIELD OF INVENTION

The present invention relates to the production of the disaccharide kojibiose which is known to be a powerful prebiotic. The invention indeed discloses the generation of genetically modified sucrose phosphorylases which convert—via a transglycosylation reaction—sucrose into kojibiose in a very efficient manner. Hence, the present invention relates to a cost-effective production method of kojibiose which is useful within industry.

BACKGROUND ART

Kojibiose (2-O-α-D-glucopyranosyl-D-glucopyranose) is a promising prebiotic for the stimulation of beneficial bacterial populations in the human gut[1, 2]. The α-1,2 bond can indeed be handled by specific micro-organisms such as Bifidobacteria, but it is largely resistant to the action of enzymes in the digestive tract[3, 4]. Moreover, kojibiose and derivatives have the ability to inhibit α-glucosidase I in different tissues and organisms[5-8]. Accordingly, these are appealing molecules because inhibitors that act upon α-glucosidase I are suggested to be interesting candidate drugs for the treatment of human immunodeficiency virus type 1 (HIV-1) infections[9]. Given their α-glucosidases inhibitory action, they can also limit the digestion of dietary carbohydrates and could therefore be useful to counter diabetes, obesity and cardiovascular diseases[10, 11]. Studies on the health-promoting properties of kojibiose are however hampered by the limited availability of this disaccharide[1]. Kojibiose is naturally present in honey[12], beer[13], sweet potato starch hydrolysate[14], sake and koji[15] (hence the name), but the amounts are too low for extraction on larger scale. According to some authors, the isolation from the partial acetolysis of dextran from *Leuconostoc mesenteroides* NRRL B-1299 is currently the best method[4, 16, 17]. Yet, it is a multi-step process involving several chemical reagents like glacial acetic acid, acetic anhydride, concentrated sulphuric acid, chloroform and methanol. Chemical synthesis via modified Koenigs-Knorr reactions is still applied as well, despite the need for multiple (de)protection steps, silver or mercury catalysts and solvents like acetonitrile, and low yields[18-20]. Alternatively, enzymes like α-glucosidase[21, 22], α-glucoamylase[22, 23], glucansucrase[24], dextransucrase[25] and kojibiose phosphorylase[4] can be used, but unfortunately these often have low yields and/or generate product mixtures. Sucrose phosphorylase (SP) is another enzyme that is capable of producing kojibiose[26, 27], starting from sucrose (renewable, cheap and readily available[28]) and D-glucose. It naturally catalyses the reversible phosphorolysis of sucrose into α-D-glucose 1-phosphate and D-fructose, but it can also glycosylate alternative acceptors with yields exceeding 90%[29, 30] (WO 2011/124538). In case of D-glucose as acceptor, the overall kojibiose yield is however lowered by the side-formation of maltose (4-O-α-D-glucopyranosyl-D-glucopyranose) as glucobiose product[27]. There is thus a need to produce a, preferably thermostable, sucrose phosphorylase having a high selectivity of kojibiose production.

SUMMARY OF THE INVENTION

The present invention relates to an isolated sucrose phosphorylase comprising an amino acid sequence given by SEQ ID N° 1 characterized in that it contains at least one of the following mutations: P134V, P134R, P134W, P134S, R135E, A193G, H234T, L341I, L343P, Y344R, Y344D, Y344V, Y344I, Q345S, Q345N and has an activity ratio of kojibiose over maltose formation greater than 0.5 during a transglycosylation reaction with glucose, or, a fragment of said sucrose phosphorylase containing at least one of said mutations and having said selectivity of kojibiose.

The present invention further relates to an isolated sucrose phosphorylase as described above containing the mutations L341I_Q345S or L341I_Y344A_Q345N and wherein said selectivity for kojibiose is characterized by a K/M ratio of 15 and 22, respectively.

The present invention further relates to an isolated nucleic acid encoding for a sucrose phosphorylase as described above, and, further relates to a vector comprising a nucleic acid as described above. Moreover, the present invention relates to a host cell comprising a vector as described above.

The present invention also relates to the usage of of a sucrose phosphorylase to produce kojibiose wherein said sucrose phosphorylase is an isolated sucrose phosphorylase comprising an amino acid sequence given by SEQ ID N° 1 characterized in that it contains at least one of the following mutations: P134V, P134R, P134W, P134S, R135E, A193G, H234T, L341I, D342A, L343P, Y344A, Y344R, Y344D, Y344V, Y344I, Q345A, Q345S, Q345N and has an activity ratio of kojibiose over maltose formation greater than 0.5 during a transglycosylation reaction with glucose, or, a fragment of said sucrose phosphorylase containing at least one of said mutations and having said selectivity of kojibiose.

The present invention relates to a process to produce kojibiose comprising the steps of:
  providing sucrose and/or alpha-glucose 1-phosphate as donor, and, glucose as acceptor,
  providing a sucrose phosphorylase as described above,
  bringing said donor and acceptor, and, said sucrose phosphorylase in a medium wherein the synthesis of kojibiose by said sucrose phosphorylase takes place, and
  purifying said kojibiose from said medium.

The present invention further relates to a process as described above wherein said purification consist of a yeast treatment.

DESCRIPTION OF THE INVENTION

The present invention relates to a systematic mutagenesis study of the active site of the sucrose phosphorylase of *Bifidobacterium adolescentis* resulting in the identification of only a few mutations that surprisingly can improve the activity ratio of kojibiose over maltose formation (K/M ratio) to values higher than 0.5. Combining mutations L341I_Y344A_Q345N into one sequence yields the highest selectivity, corresponding to a K/M ratio of 22. However, the double mutant L341I_Q345S produces kojibiose two times faster than this triple mutant and has a K/M ratio of 15, which is still enough to generate highly pure kojibiose. A further and simple purification procedure consists of a yeast treatment to consume the remaining glucose, fructose and sucrose.

Hence, the present invention relates to an isolated sucrose phosphorylase comprising an amino acid sequence given by SEQ ID N° 1 characterized in that it contains at least one of the following mutations: P134V, P134R, P134W, P134S, R135E, A193G, H234T, L341I, D342A, L343P, Y344A, Y344R, Y344D, Y344V, Y344I, Q345A, Q345S and Q345N and having a K/M ratio of kojibiose over maltose formation greater than 0.5 during a transglycosylation reaction with glucose as acceptor, or, a fragment of said sucrose phosphorylase containing at least one said mutations and having said selectivity of kojibiose.

More specifically, the present invention relates to an isolated sucrose phosphorylase comprising an amino acid sequence given by SEQ ID N° 1 characterized in that it contains at least one of the following mutations: P134V, P134R, P134W, P134S, R135E, A193G, H234T, L341I, L343P, Y344R, Y344D, Y344V, Y344I, Q345S, Q345N and has an activity ratio of kojibiose over maltose formation greater than 0.5 during a transglycosylation reaction with glucose, or, a fragment of said sucrose phosphorylase containing at least one of said mutations and having said selectivity of kojibiose.

The term 'sucrose phosphorylase comprising an amino acid sequence given by SEQ ID N° 1' refers to an amino acid sequence comprising an amino acid sequence encoded by a nucleic acid having GenBank accession Number AF543301 as described by Sprogoe et al. (2004). The latter nucleic acid corresponds to a sucrose phosphorylase gene from *Bifidobacterium adolescentis*. More specifically, the latter term refers to a sucrose phosphorylase encoded by the sucrose phosphorylase gene from *Bifidobacterium adolescentis* LMG 10502 as described by Reuter (1963) and which is synonymous to DSM20083 and ATTC15703. SEQ ID N° 1 corresponds to the following amino acid sequence (the amino acids of which at least one should be substituted according to the present invention are underlined):

MKNKVQLITYADRLGDGTIKSMTDILRTRFDGVYDGVHILPFFTPFDGA

DAGFDPIDHTKVDERLGSWDDVAELSKTHNIMVDAIVNHMSWESKQFQD

VLAKGEESEYYPMFLTMSSVFPNGATEEDLAGIYRPRPGLPFTHYKFAG

KTRLVWVSFTPQQVDIDTDSDKGWEYLMSIFDQMAASHVSYIRLDAVGY

GAKEAGTSCFMTPKTFKLISRLREEGVKRGLEILIEVHSYYKKQVEIAS

KVDRVYDFALPPLLLHALSTGHVEPVAHWTDIRPNNAVTVLDTHDGIGV

IDIGSDQLDRSLKGLVPDEDVDNLVNTIHANTHGESQAATGAAASNLDL

YQVNSTYYSALGCNDQHYIAARAVQFFLPGVPQVYYVGALAGKNDMELL

RKTNNGRDINRHYYSTAEIDENLKRPVVKALNALAKFRNELDAFDGTFS

YTTDDDTSISFTWRGETSQATLTFEPKRGLGVDNTTPVAMLEWEDSAGD

HRSDDLIANPPVVA

The terms "characterized in that it contains at least one of the following mutations: P134V, P134R, P134W, P134S, R135E, A193G, H234T, L341I, D342A, L343P, Y344A, Y344R, Y344D, Y344V, Y344I, Q345A, Q345S and Q345N" refers to the fact that specific amino acids at specific positions of wild type SEQ ID N° 1 (i.e. at amino acid positions 134, 135, 193, 234, 341, 342, 343, 344 and/or 345) have been substituted by other specific amino acids. The latter substitutions can be obtained by any method known in the art. The latter method can be for example mutating, via for example performing site-directed mutagenesis, the sucrose phosphorylase gene from *Bifidobacterium adolescentis*. The term "at least one of the following mutations" indicates that the mutant sucrose phosphorylase of the present invention must contain one of the indicated list of single mutations but may also contain 2, 3, 4, . . . , 16, 17 or all of the in total 18 single mutations, or, any combination of said list of single mutations which results in mutant sucrose phosphorylases containing multiple (i.e. 2, 3, 4, 5, 6, 7, 8, 9, 10 . . . ) mutations. Preferred —but non-limiting— examples of specific combinations of 2, 3, 4, 5, 6 and 7 of said list of mutations are given in Table 1.

The terms "having an activity ratio of kojibiose over maltose formation greater than 0.5 during a transglycosylation reaction with glucose as acceptor" refers to the fact that sucrose phosphorylases are capable of producing kojibiose[26, 27], starting from sucrose and D-glucose. It naturally catalyses the reversible phosphorolysis of sucrose into α-D-glucose 1-phosphate and D-fructose, but it can also glycosylate alternative acceptors with yields exceeding 90%[29, 30] (WO 2011/124538). In case of D-glucose as acceptor, the overall kojibiose yield is however lowered by the side-formation of maltose (4-O-α-D-glucopyranosyl-D-glucopyranose) as glucobiose product[27]. For example, the wild-type and thermostable SP from *Bifidobacterium adolescentis* (WO 2011/124538) displays a K/M ratio of only 0.5, meaning that the velocity of maltose formation is twice as high as the velocity of kojibiose formation. The mutants of the present invention as indicated above have a K/M ratio that is greater than 0.5 (i.e. 0.6, 0.7, 0.8, 0.9, 1.0, . . . , 2.0 . . . , 3.0 . . . , 4.0, . . . 10.0, . . . 20.0, . . . 30.0 . . . ) meaning that the mutants show a velocity of formation of kojibiose that is increased relative to the velocity of maltose formation, when compared to the wild-type enzyme.

The terms "a fragment of said sucrose phosphorylase containing at least one said mutations and having said selectivity of kojibiose" refers to a protein (or peptide or polypeptide) containing fewer amino acids than the amino acid sequence as depicted by SEQ ID N° 1 and that retains the activity of said mutant sucrose phosphorylases of the present invention (i.e. the velocity of kojibiose formation is increased relative to the velocity of maltose formation when compared to the wild-type enzyme). Such fragment must thus contain at least one of the indicated list of single mutations or a combination thereof as indicated above and can—for example—be a protein with a deletion of 10% or less of the total number of amino acids at the C- and/or N-terminus.

The present invention preferably relates to mutants of the present invention have a K/M ratio that is greater than 10.0 (i.e. 10.0, . . . 15.0, . . . 20.0 . . . ) meaning that the mutants show a velocity of formation of kojibiose and a velocity of maltose formation which is significantly higher and lower, respectively compared to corresponding velocities of the wild-type enzyme.

Hence, and more specifically, the present invention relates to an isolated sucrose phosphorylase as described above containing the mutations L341I_Q345S or L341I_Y344A_Q345N and wherein said selectivity for kojibiose is characterized by a K/M ratio of 15 and 22, respectively.

The present invention further relates to an isolated nucleic acid encoding for a sucrose phosphorylase as described above. An example of a nucleic acid encoding for mutant sucrose phosphorylase of the present invention (SEQ ID N° 2) is as follows (the codons of which at least one should be mutated according to the present invention are underlined):

ATGAAAAATAAAGTCCAACTGATTACCTATGCGGATCGTCTGGGTGATG

GCACCATTAAAAGCATGACGGACATCCTGCGTACCCGCTTTGATGGCGT

TTATGACGGTGTCCACATTCTGCCGTTTTTCACCCCGTTTGATGGCGCC

-continued
```
GACGCAGGTTTCGATCCGATCGACCATACCAAAGTTGATGAACGTCTGG

GTAGCTGGGATGACGTCGCCGAACTGTCTAAAACCCACAACATTATGGT

GGATGCAATCGTTAATCACATGTCATGGGAATCGAAACAGTTCCAAGAT

GTTCTGGCCAAAGGCGAAGAATCAGAATATTACCCGATGTTTCTGACCA

TGAGCAGCGTGTTCCCGAACGGTGCCACGGAAGAAGACCTGGCAGGCAT

TTATCGTCCGCGTCCGGGTCTGCCGTTTACCCACTACAAATTCGCAGGC

AAAACGCGTCTGGTCTGGGTGTCTTTTACCCCGCAGCAAGTGGACATCG

ATACGGACAGTGATAAAGGTTGGGAATATCTGATGTCCATTTTCGACCA

AATGGCGGCCAGCCATGTGTCTTATATCCGCCTGGATGCGGTTGGCTAC

GGTGCCAAAGAAGCAGGCACCAGTTGCTTTATGACCCCGAAAACGTTCA

AACTGATTTCCCGTCTGCGCGAAGAAGGCGTGAAACGCGGTCTGGAAAT

TCTGATCGAAGTCCACAGCTATTACAAAAAACAGGTGGAAATCGCGTCT

AAAGTGGATCGCGTTTATGACTTTGCCCTGCCGCCGCTGCTGCTGCATG

CCCTGAGTACCGGCCACGTCGAACCGGTGGCCCATTGGACGGATATTCG

TCCGAACAATGCTGTTACCGTCCTGGATACGCATGACGGCATCGGCGTT

ATTGATATCGGTTCAGATCAGCTGGACCGCTCGCTGAAAGGTCTGGTGC

CGGACGAAGATGTGGATAACCTGGTGAATACGATTCATGCGAACACCCA

CGGCGAATCACAGGCAGCTACCGGTGCGGCGGCATCGAACATTGATCTG

TACTCGGTTAATAGTACCTACTACTCCGCTCTGGGCTGTAACGATCAGC

ACTACATCGCTGCGCGTGCGGTGCAGTTTTTCCTGCCGGGTGTTCCGCA

AGTCTATTACGTGGGCGCCCTGGCAGGTAAAAATGATATGGAACTGCTG

CGCAAAACCAACAATGGTCGTGACATTAACCGCCATTATTACAGCACGG

CCGAAATCGATGAAAATCTGAAACGTCCGGTGGTTAAAGCACTGAACGC

TCTGGCGAAATTTCGCAATGAACTGGATGCTTTTGACGGCACCTTCTCA

TATACCACGGATGACGATACGAGTATTTCCTTTACCTGGCGTGGTGAAA

CGTCGCAGGCCACCCTGACGTTCGAACCGAAACGCGGCCTGGGTGTTGA

TAATACCACGCCGGTCGCAATGCTGGAATGGGAAGACAGTGCTGGTGAC

CATCGCTCCGACGACCTGATCGCTAATCCGCCGGTTGTTGCG
```

The present invention also relates to a vector comprising a nucleic acid as described above.

The present invention further relates to a host cell comprising a vector as described above.

The term 'nucleic acid' as used herein corresponds to the sucrose phosphorylase gene from *Bifidobacterium adolescentis*, and preferably from *Bifidobacterium adolescentis* LMG 10502. Said nucleic acids can be incorporated in appropriate vectors such as plasmids and appropriate host cells such as *Escherichia coli* can be transfected with said vectors.

The present invention relates to the usage of a sucrose phosphorylase as described above to produce kojibiose.

More specifically, the present invention relates to the usage of a sucrose phosphorylase to produce kojibiose wherein said sucrose phosphorylase is an isolated sucrose phosphorylase comprising an amino acid sequence given by SEQ ID N° 1 characterized in that it contains at least one of the following mutations: P134V, P134R, P134W, P1345, R135E, A193G, H234T, L341I, D342A, L343P, Y344A, Y344R, Y344D, Y344V, Y344I, Q345A, Q345S, Q345N and has an activity ratio of kojibiose over maltose formation greater than 0.5 during a transglycosylation reaction with glucose, or, a fragment of said sucrose phosphorylase containing at least one of said mutations and having said selectivity of kojibiose.

More specifically, the present invention relates to a process to produce kojibiose comprising the steps of:
providing sucrose and/or alpha-glucose 1-phosphate as donor, and, glucose as acceptor,
providing a sucrose phosphorylase as described above,
bringing said donor and acceptor, and, said sucrose phosphorylase in a medium wherein the synthesis of kojibiose by said sucrose phosphorylase takes place, and
purifying said kojibiose from said medium.

The term providing sucrose and/or alpha-glucose 1-phosphate as donor means that sucrose or alpha-glucose 1-phosphate or a mixture of both may be used as donor in order to glucosylate the acceptor glucose via the mutant sucrose phosphorylases of the present invention.

The term providing a sucrose phosphorylase means providing a mutant sucrose phosphorylase of the present invention. A non-limiting example of the latter 'providing' encompasses: a) mutating the sucrose phosphorylase wt gene from *Bifidobacterium adolescentis* contained in a vector such as a plasmid, b) transforming a host cell such as *E. coli* with said mutated genes, c) checking the desired mutations by sequencing each construct, d) growing individual colonies, e) lysing said colonies and f) purifying the mutant sucrose phosphorylases of interest.

The term 'medium' refers to any suitable medium known in the art which allows—when the mutant enzyme of the present invention, acceptor and donor are added to said medium—the synthesis of kojibiose by a sucrose phosphorylase of the present invention. An example of such a medium is the 3-(N-morpholino)propanesulfonic acid (MOPS) buffer.

The term "purifying" relates to any purification method known in the art but preferably relates to a purification consisting of a yeast treatment such as a treatment with baker's yeast.

The present invention thus specifically relates to a process as described above wherein said purification consists of a yeast treatment. After said treatment, the yeast can be removed via centrifugation and the supernatant can be evaporated. The kojibiose solution can then be cooled down in order to obtain pure kojibiose crystals which can be washed with ethanol.

The present invention will further be illustrated by the following non-limiting example.

EXAMPLE

Engineering of Sucrose Phosphorylase for the Selective Production of Kojibiose

Methods and Materials

Mutagenesis was performed on the constitutive expression plasmid pCXP34h[31] containing the sucrose phosphorylase gene from *Bifidobacterium adolescentis* LMG 10502. Saturation libraries were generated using either the Quikchange[TM32] protocol or the protocol described by Sanchis et al.[33], while site-directed mutagenesis was performed with the latter. In all cases, the mutated DNA was transformed in *E. coli* CGSC 8974 (Coli Genetic Stock Center, New Haven, Conn., USA). For each library, the constructs were subjected to nucleotide sequencing (AGOWA Sequence Service, Berlin, Germany) in order to confirm that the desired mutations were indeed introduced and to exclude the presence of undesirable mutations.

Individual colonies were picked, grown and lysed as described previously[34], with the difference that the lysis buffer composition was altered (1 mg/ml lysozyme, 0.1 mM PMSF, 50 mM $Na_2SO_4$, 4 mM $MgSO_4$ and 1 mM EDTA in 50 mM MOPS buffer pH 7.0). Screening was performed by incubating crude cell extract with substrate solution in low well microtiter plates at 37° C. Interesting mutants were then produced at Erlenmeyer scale and purified by Ni-affinity chromatography[35] for further characterization at a temperature of 58° C. All reactions were performed with a donor concentration of 100 mM (sucrose or α-D-glucose 1-phosphate) and acceptor concentration of 200 mM (glucose) and were analysed by High Performance Anion Exchange Chromatography with Pulsed Amperometric Detection (HPAEC-PAD) (Dionex ICS-3000, Thermo Scientific). The K/M ratio was defined as the ratio of initial velocity of kojibiose formation and the initial velocity of maltose formation.

The production of kojibiose was performed by incubating 2 mg/mL of mutant L341I_Q345S with 0.5M sucrose and 0.5M glucose in 0.1 L of MOPS buffer at pH 7 and 55° C. for 24 h, after which the enzyme was inactivated by heating the mixture to 95° C. during 10 min. Next, the pH was adjusted to 5, and 30 g/L baker's yeast (Algist Bruggeman) was added. After 8 h incubation at 30° C. and 50 rpm on a rotary shaker, the yeast was removed by centrifugation (5 000 g, 4° C., 20 min), and the obtained supernatant was evaporated at 50° C. to a brix of 48 (Atago hand refractometer) using a rotary evaporator (Buchi, Rotavapor R-134). Next, the kojibiose solution was slowly cooled to 22° C. over a period of 4 h, and subsequently stored during 16 h at 22° C. The obtained crystals were washed with ethanol (3 times 10 mL), and dried during 24 h in vacuo. The purity of the obtained crystals was analysed by HPAEC-PAD (Dionex ICS-3000, Thermo Scientific) and Ion-Moderated Partition chromatography (aminex HPX-87H, Bio-Rad).

Results

First, several active site residues (Y132, P134, R135, Y196, V233, L341, D342, L343, Y344, Q345) were one by one mutated to alanine to evaluate their influence on product specificity. To that end, the K/M ratio of kojibiose and maltose formation was measured for each of the single mutants and compared with that of the wild-type enzyme. In some cases the preference for maltose formation was enhanced (like for Y196A), but for other mutants the opposite was true (e.g. P134A, D342A, Y344A and Q345A). This shows that predicting changes in product specificity is not a trivial task. Interestingly, all enzymes were still active with both sucrose and glucose 1-phosphate as glycosyl donor, meaning that their donor selectivity was not fundamentally altered.

Next, several active site positions were submitted to site-saturation mutagenesis to identify the best single mutants for kojibiose production (Table 1). The best mutant was found to be L341I, which displays a K/M ratio of 3.9 (formation of kojibiose over maltose). To further improve the enzyme's specificity, the best single mutant L341I was combined with the next best mutations, i.e. P134V, Q345S and Q345N. Surprisingly, the combination with of Q345N or Q345S increased the K/M ratio to 15-18, whereas the combination with P134V decreased the K/M ratio. The specificity of the double mutant L341I_Q345N was further optimised by introducing an alanine at position 344, resulting in a K/M ratio of 22. Combining more than 3 mutations was also attempted but no further improvements in K/M ratio could be observed (Table 1).

TABLE 1

Characterization of several mutants of sucrose phosphorylase

| enzyme | kojibiose formation (U/mg)[#] | K/M ratio |
| --- | --- | --- |
| wild-type | 0.152 | 0.5 |
| Y132A | 0.039 | 0.4 |
| R135A | 0.138 | 0.6 |
| V233A | 0.145 | 0.6 |
| L341A | 0.056 | 0.4 |
| D342A | 0.050 | 0.9 |
| L343A | 0.130 | 0.4 |
| Y344A | 0.210 | 1.0 |
| Q345A | 0.112 | 1.0 |
| Y132A | 0.039 | 0.4 |
| R135A | 0.138 | 0.6 |
| P134V | 0.136 | 2.2 |
| P134R | 0.016 | 1.6 |
| P134W | 0.028 | 2.8 |
| P134T | 0.113 | 0.6 |
| P134S | 0.072 | 1.1 |
| R135E | 0.018 | 0.8 |
| R135P | 0.010 | 0.2 |
| R135V | 0.038 | 0.6 |
| A193G | 0.090 | 1.1 |
| A193S | 0.019 | 0.3 |
| A193T | 0.002 | 0.3 |
| A193V | 0.001 | 0.5 |
| H234T | 0.003 | 1.0 |
| L341I | 0.372 | 3.9 |
| L343P | 0.023 | 1.1 |
| Y344F | 0.123 | 0.6 |
| Y344R | 0.069 | 0.8 |
| Y344D | 0.051 | 0.7 |
| Y344V | 0.074 | 1.2 |
| Y344I | 0.038 | 1.6 |
| Q345S | 0.138 | 2.2 |
| Q345N | 0.010 | 2.6 |
| L341I_Q345S | 0.100 | 14.9 |
| L341I_Q345N | 0.048 | 18.3 |
| P134V_L341I | 0.241 | 1.8 |
| P134V_Q345S | 0.145 | 3.9 |
| P134V_Q345N | 0.051 | 6.0 |
| P134V_L341I_Q345S | 0.173 | 6.7 |
| P134V_L341I_Q345N | 0.093 | 12.4 |
| L341I_Y344A_Q345N | 0.058 | 22.3 |
| L341I_Y344I_Q345N | 0.052 | 15.2 |
| P134V_L341_Y344I_Q345N | 0.056 | 7.5 |
| P134V_L341I_L343P_Y344I_Q345N | 0.011 | 7.2 |
| P134V_L341I_L343P_Y344V_Q345N | 0.018 | 8.6 |
| P134V_R135E_L341I_Y344I_Q345N | 0.016 | 5.0 |
| P134V_L341_D342A_Y344I_Q345N | 0.001 | 4.4 |
| P134V_L341I_D342A_L343P_Y344I_Q345N | 0.003 | 6.7 |
| P134V_R135V_L341I_L343P_Y344I_Q345N | 0.006 | 5.1 |

[#]activity measurements had a coefficient of variation (CV) of less than 10%

To demonstrate the practical usefulness of the obtained mutants, the production of kojibiose was performed at a larger scale (0.1 L) and with higher substrate concentrations (0.5M sucrose and 0.5M glucose), which is preferred by the industry. To that end, the double mutant L341I/Q345S was employed as it displays a good balance between activity and product specificity. After incubating 2 mg/mL of enzyme with the substrates for 24 h, the reaction was terminated by heating to 95° C. and contaminating carbohydrates were removed by yeast treatment. Finally, the solution was concentrated and then slowly cooled to induce crystallization. In that way, 12.4 g of crystalline kojibiose with a purity exceeding 99% could be obtained. When the wild-type enzyme was incubated under similar conditions, only 2.7 g of kojibiose was produced and we were unable to crystallize this disaccharide from the product mixture.

REFERENCES

1. Sanz, M. L., Gibson, G. R. & Rastall, R. A. (2005) Influence of disaccharide structure on prebiotic selectivity in vitro. *Journal of Agricultural and Food Chemistry* 53(13):5192-5199
2. Nakada, T., Nishimoto, T., Chaen, H. & Fukuda, S. in Oligosaccharides in Food and Agriculture, Vol. 849 104-117 (American Chemical Society, 2003).
3. Djouzi, Z., Andrieux, C., Pelenc, V. et al. (1995) Degradation and fermentation of alpha-gluco-oligosaccharides by bacterial strains from human colon—in vitro and in vivo studies in gnotobiotic rats. *Journal of Applied Bacteriology* 79(2):117-127
4. Chaen, H., Nishimoto, T., Nakada, T. et al. (2001) Enzymatic synthesis of kojioligosaccharides using kojibiose phosphorylase. *Journal of Bioscience and Bioengineering* 92(2):177-182
5. Ugalde, R. A., Staneloni, R. J. & Leloir, L. F. (1980) Mirosomal glucosidases of rat liver—partial purification and inhibition by disaccharides. *European Journal of Biochemistry* 113(1):97-103
6. Shailubhai, K., Pratta, M. A. & Vijay, I. K. (1987) Purification and characterization of glucosidase I involved in N-linked glycoprotein processing in bovine mammary gland. *Biochemical Journal* 247(3):555-562
7. Szumilo, T., Kaushal, G. P. & Elbein, A. D. (1986) Purification and properties of glucosidase I from mung bean seedlings. *Archives of Biochemistry and Biophysics* 247(2):261-271
8. Bause, E., Erkens, R., Schweden, J. & Jaenicke, L. (1986) Purification and characterization of trimming glucosidase I from *Saccharomyces cerevisiae*. *FEBS Letters* 206(2):208-212
9. Borges de Melo, E., da Silveira Gomes, A. & Carvalho, I. (2006) α- and β-Glucosidase inhibitors: chemical structure and biological activity. *Tetrahedron* 62(44):10277-10302
10. Standl, E. & Schnell, O. (2012) Alpha-glucosidase inhibitors 2012-cardiovascular considerations and trial evaluation. *Diabetes and Vascular Disease Research* 9(3):163-169
11. Phung, O. J., Scholle, J. M., Talwar, M. & Coleman, C. I. (2010) Effect of Noninsulin Antidiabetic Drugs Added to Metformin Therapy on Glycemic Control, Weight Gain, and Hypoglycemia in Type 2 Diabetes. *Jama-Journal of the American Medical Association* 303(14):1410-1418
12. Watanabe, T. & Aso, K. (1959) Isolation of kojibiose from honey. *Nature* 183(4677):1740-1740
13. Hough, J. S., Briggs, D. E., Stevens, R. & Young, T. W. in Malting and Brewing Science, Volume II Hopped Word and Beer 776-838 (Chapman and Hall Ltd., New York, USA; 1982).
14. Sato, A. & Aso, K. (1957) Kojibiose (2-O-alpha-D-glucopyranosyl-D-glucose)—isolation and structure—isolation for hydrol. *Nature* 180(4593):984-985
15. Matsuda, K. (1959) Studies on the disaccharides in koji extract and sake. V. Isolation and identification of kojibiose. *Nippon Nogeikagaku Kaishi*33):719-723
16. Matsuda, K., Watanabe, H., Fujimoto, K. & Aso, K. (1961) Isolation of nigerose and kojibiose from dextrans. *Nature* 191(478):278
17. Duke, J., Little, N. & Goldstein, I. J. (1973) Preparation of cyrstalline α-kojibiose octaacetate from dextran B-1299-S: Its conversion into p-nitrophenyl and p-isothiocyanatophenyl β-kojibioside. *Carbohydrate Research* 27(1):193-198
18. Igarashi, K., Irisawa, J. & Honma, T. (1975) Syntheses of α-D-linked disaccharides. *Carbohydrate Research* 39(2):341-343
19. Wolfrom, M. L., Lineback, D. R. & Thompson, A. (1963) Isopropyl tetra-O-acetyl-alpha-D-glucopyranoside—a synthesis of kojibiose. *Journal of Organic Chemistry* 28(3):860
20. Helferich, B. & Zirner, J. (1962) Zur synthese von tetraacetyl-hexosen mit freiem 2-hydroxyl—synthese einiger disaccharide. *Chemische Berichte-Recueil* 95(11):2604
21. Takahash. M, Shimomur. T & Chiba, S. (1969) Biochemical studies on buckwheat alpha-glucosidase. 3. Transglucosylation action of enzyme and isolation of reaction products. *Agricultural and Biological Chemistry* 33(10):1399
22. Fujimoto, H., Nishida, H. & Ajisaka, K. (1988) Enzymatic syntheses of glucobioses by a condensation reaction with alpha-glucosidase, beta-glucosidase and glucoamylase. *Agricultural and Biological Chemistry* 52(6):1345-1351
23. Cantarella, L., Nikolov, Z. L. & Reilly, P. J. (1994) Dissaccharide production by glucoamylase in aqueous ether mixtures. *Enzyme and Microbial Technology* 16(5):383-387
24. Brison, Y., Pijning, T., Malbert, Y. et al. (2012) Functional and Structural Characterization of α-(1→2) Branching Sucrase Derived from DSR-E Glucansucrase. *Journal of Biological Chemistry* 287(11):7915-7924
25. Diez-Municio, M., Montilla, A., Javier Moreno, F. & Herrero, M. (2014) A sustainable biotechnological process for the efficient synthesis of kojibiose. *Green Chemistry* 16(4):2219-2226
26. Kitao, S., Yoshida, S., Horiuchi, T., Sekine, H. & Kusakabe, I. (1994) Formation of Kojibiose and Nigerose by Sucrose Phosphorylase. *Bioscience Biotechnology and Biochemistry* 58(4):790-791
27. Goedl, C., Sawangwan, T., Brecker, L., Wildberger, P. & Nidetzky, B. (2010) Regioselective O-glucosylation by sucrose phosphorylase: a promising route for functional diversification of a range of 1,2-propanediols. *Carbohydrate Research* 345(12):1736-1740
28. Skov, L. K., Mirza, O., Sprogoe, D. et al. (2006) Crystal structure of the Glu328Gln mutant of *Neisseria polysaccharea* amylosucrase in complex with sucrose and maltoheptaose. *Biocatalysis and Biotransformation* 24(1-2):99-105
29. Desmet, T. & Soetaert, W. (2011) Broadening the synthetic potential of disaccharide phosphorylases through enzyme engineering. *Process Biochemistry* 47(1):11-17
30. Desmet, T., Soetaert, W., Bojarova, P. et al. (2012) Enzymatic Glycosylation of Small Molecules: Challenging Substrates Require Tailored Catalysts. *Chemistry-a European Journal* 18(35):10786-10801
31. Aerts, D., Verhaeghe, T., De Mey, M., Desmet, T. & Soetaert, W. (2011) A constitutive expression system for high-throughput screening. *Engineering in Life Sciences* 11(1):10-19
32. Hogrefe, H. H., Cline, J., Youngblood, G. L. & Allen, R. M. (2002) Creating randomized amino acid libraries with the QuikChange (R) Multi Site-Directed Mutagenesis Kit. *BioTechniques* 33(5):1158

33. Sanchis, J., Fernandez, L., Carballeira, J. et al. (2008) Improved PCR method for the creation of saturation mutagenesis libraries in directed evolution: application to difficult-to-amplify templates. *Applied Microbiology and Biotechnology* 81(2):387-397
34. Verhaeghe, T., Diricks, M., Aerts, D. et al. (2013) Mapping the acceptor site of sucrose phosphorylase from *Bifidobacterium adolescentis* by alanine scanning. *Journal of Molecular Catalysis B: Enzymatic*, 96:81-88
35. Aerts, D., Verhaeghe, T. F., Roman, B. I. et al. (2011) Transglucosylation potential of six sucrose phosphorylases toward different classes of acceptors. *Carbohydrate Research* 346(13):1860-1867
36. Lee, J. H., Yoon, S. H., Nam, S. H. et al. (2006) Molecular cloning of a gene encoding the sucrose phosphorylase from *Leuconostoc mesenteroides* B-1149 and the expression in *Escherichia coli*. *Enzyme and Microbial Technology* 39(4):612-620
37. Verhaeghe, T., Aerts, D., Diricks, M. et al. (2014) The quest for a thermostable sucrose phosphorylase reveals sucrose 6'-phosphate phosphorylase as a novel specificity. *Applied Microbiology and Biotechnology*, 98(16): 7027-7037

The invention claimed is:

1. An isolated sucrose phosphorylase mutant of a single phosphorylase having the amino acid sequence of SEQ ID NO:1, wherein said mutant consists of at least one of the following substitutions in SEQ ID NO:1: P134V, P134R, P134W, P134S, R135E, A193G, H234T, L341I, L343P, Y344R, Y344D, Y344V, Y344I, Q345S, Q345N and has an activity ratio of kojibiose over maltose formation greater than 0.5 during a transglycosylation reaction with glucose.

2. An isolated sucrose phosphorylase mutant of a single phosphorylase having the amino acid sequence of SEQ ID NO:1, wherein the mutant consists of the mutations L341I_Q345S or L341I_Y344A_Q345N and wherein said selectivity for kojibiose is characterized by a K/M ratio of 15 and 22, respectively.

3. An isolated nucleic acid encoding for a sucrose phosphorylase mutant according to claim 1.

4. A vector comprising a nucleic acid according to claim 3.

5. A host cell comprising a vector according to claim 4.

6. A process to produce kojibiose comprising the steps of:
providing sucrose and/or alpha-glucose 1-phosphate as donor, and, glucose as acceptor,
providing a sucrose phosphorylase mutant as defined by claim 1,
bringing said donor and acceptor, and, said sucrose phosphorylase in a medium wherein the synthesis of kojibiose by said sucrose phosphorylase takes place, and
purifying said kojibiose from said medium.

7. A process according to claim 6 wherein said purification consist of a yeast treatment.

8. An isolated nucleic acid encoding for a sucrose phosphorylase mutant according to claim 2.

9. A vector comprising a nucleic acid according to claim 8.

10. A host cell comprising a vector according to claim 9.

* * * * *